(12) United States Patent
Semperlotti et al.

(10) Patent No.: US 9,437,183 B2
(45) Date of Patent: Sep. 6, 2016

(54) METAMATERIAL BASED ACOUSTIC LENSES FOR STRUCTURAL HEALTH MONITORING

(71) Applicant: University of Notre Dame du Lac, Notre Dame, IN (US)

(72) Inventors: Fabio Semperlotti, Granger, IN (US); Hongfei Zhu, South Bend, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 0 days.

(21) Appl. No.: 14/577,556

(22) Filed: Dec. 19, 2014

(65) Prior Publication Data

US 2015/0228269 A1 Aug. 13, 2015

Related U.S. Application Data

(60) Provisional application No. 61/918,516, filed on Dec. 19, 2013.

(51) Int. Cl.
*G10K 11/30* (2006.01)
*G01N 29/22* (2006.01)
*G01N 29/04* (2006.01)
*G10K 11/26* (2006.01)

(52) U.S. Cl.
CPC ............ *G10K 11/30* (2013.01); *G01N 29/04* (2013.01); *G01N 29/221* (2013.01); *G01N 2291/0231* (2013.01); *G01N 2291/0258* (2013.01); *G01N 2291/02491* (2013.01); *G01N 2291/042* (2013.01); *G01N 2291/106* (2013.01)

(58) Field of Classification Search
CPC ............ G01N 29/04; G01N 29/221; G01N 2291/0231; G01N 2291/02491; G01N 2291/0258; G01N 2291/042; G01N 2291/106; G10K 11/30

USPC ........................................................ 181/176
See application file for complete search history.

(56) References Cited

U.S. PATENT DOCUMENTS

| | | | |
|---|---|---|---|
| 7,733,198 B1 * | 6/2010 | Olsson | G10K 11/20 333/187 |
| 8,819,904 B2 * | 9/2014 | Gorisse | H01L 21/0337 29/25.35 |
| 8,833,510 B2 * | 9/2014 | Koh | F16F 15/02 181/207 |
| 9,058,798 B2 * | 6/2015 | Walker | G10K 11/00 |
| 9,084,057 B2 * | 7/2015 | Turqueti | H04R 1/326 |
| 9,199,217 B2 * | 12/2015 | Sinha | B01J 19/06 |
| 2013/0214878 A1 * | 8/2013 | Gorisse | H03H 9/0033 333/187 |
| 2015/0316511 A1 * | 11/2015 | Guo | G01N 29/2418 398/140 |

FOREIGN PATENT DOCUMENTS

KR 20130051696 A * 5/2013

* cited by examiner

*Primary Examiner* — Edgardo San Martin
(74) *Attorney, Agent, or Firm* — Greenberg Traurig, LLP

(57) ABSTRACT

An embedded acoustic metamaterial lenses allows for ultrasonic beam-forming and high resolution identification of acoustic sources for structural health monitoring. The lenses design provides an alternative to conventional phased-array technology enabling the formation of steerable and collimated (or focused) ultrasonic beams by exploiting a single transducer. The ultrasonic beam can be steered by simply tuning the frequency of the excitation. Also, the embedded lens can be designed to achieve sub-wavelength resolution to clustered acoustic sources which is a typical scenario encountered in incipient structural damage.

4 Claims, 3 Drawing Sheets

METAMATERIAL BASED ACOUSTIC LENSES FOR STRUCTURAL HEALTH MONITORING

CROSS REFERENCE TO RELATED APPLICATION

This application is a non-provisional application claiming priority from U.S. Provisional Application Ser. No. 61/918,516, filed Dec. 19, 2013, entitled "Metamaterial Based Acoustic Lenses for Structural Health Monitoring" and incorporated herein by reference in its entirety.

FIELD OF THE DISCLOSURE

The present description relates generally to high resolution identification of acoustic sources, and more particularly to metamaterial based acoustic lenses for structural health monitoring.

BACKGROUND OF RELATED ART

The process of implementing a damage detection and characterization strategy for engineering structures is referred to as Structural Health Monitoring (SHM). Here damage is defined as changes to the material and/or geometric properties of a structural system, including changes to the boundary conditions and system connectivity, which adversely affect the system's performance. The SHM process involves the observation of a system over time using periodically sampled dynamic response measurements from an array of sensors, the extraction of damage-sensitive features from these measurements, and the statistical analysis of these features to determine the current state of system health.

Selective interrogation is considered as a critical enabling technology for the implementation of the next generation of ultrasonic based Structural Health Monitoring systems. The ability to send ultrasonic energy in a preferential direction leads to increased damage sensitivity due to improved interaction (either in terms of back-scattered echo for a linear damage or of the nonlinear harmonic amplitude for nonlinear incipient damage) between the interrogation signal and the damage. In highly directional or anisotropic material, such as for layered composite structures, the direction of energy propagation can be largely different from the original direction of the interrogation signal. This situation results in reduced damage sensitivity because only a fraction of the incident wave energy can effectively reach the damage. The ability to generate highly directional and collimated signals can be exploited to compensate for this intrinsic characteristic of the material. In case of a multiple damage scenario, a directional interrogation would also allow to selectively scan the structural element and acquire data from the individual damage, which will increase the sensitivity and provide additional information for damage localization.

To-date, one of the most diffused approach to achieve selective interrogation for SHM applications has certainly been based on Phased-Arrays (PA) technology. PA exploits a set of transducers activated according to pre-defined time delays in order to produce either directional wavefronts or focused excitation at a prescribed spatial location. Although a robust and, to some extent, effective technology PA exhibits two important limitations that prevent its extensive use in practical applications. The first limitation consists in the large number of transducers required for implementation. The need for an extended transducer network is regarded as a major limitation in SHM applications because strictly related to increased probability of false alarms and hardware malfunctions as well as higher system complexity that affects fabrication and installation (e.g. harnessing, powering, etc.). The second major drawback of PA technology is related to its inability to generate collimated signals. In PAs, either the directional or focused excitation is the result of constructive interference produced by the superposition of multiple omni-directional wavefronts. In a multiple damage scenario, these wavefronts produce multiple reflected echoes (although weaker than those generated at the focal point) that reduce the accuracy of the detection. Note that, when multiple damages are closely spaced together (i.e. clustered damage) the damage signature does not provide the level of spatial resolution necessary to discern the individual damage. This situation typically results in an overestimated damage footprint and in lack of information about the damage shape.

DETAILED DESCRIPTION

The following description of example methods and apparatus is not intended to limit the scope of the description to the precise form or forms detailed herein. Instead the following description is intended to be illustrative so that others may follow its teachings.

The ability to create directional and collimated ultrasonic beams (as provided by the use of embedded metamaterial lenses) may benefit the damage detection and localization process in presence of multiple damage by enabling a selective scan of prescribed structural areas. This process would typically produce reflected echoes only from selected damage, therefore reducing unwanted back-scattering from other sources. In the present disclosure, an approach targeted to address the above-identified issues during both the interrogation and sensing phase is presented. In particular, the present disclosure develops a selective interrogation technique that may overcome the limitations of PAs by producing highly collimated (or focused), steerable ultrasonic beams by using a single transducer. The disclosure also discloses that the same technology can be used to increase the sensitivity to clustered acoustic sources, characteristic of an incipient damage scenario, by enabling sub-wavelength resolution.

Figure 1:
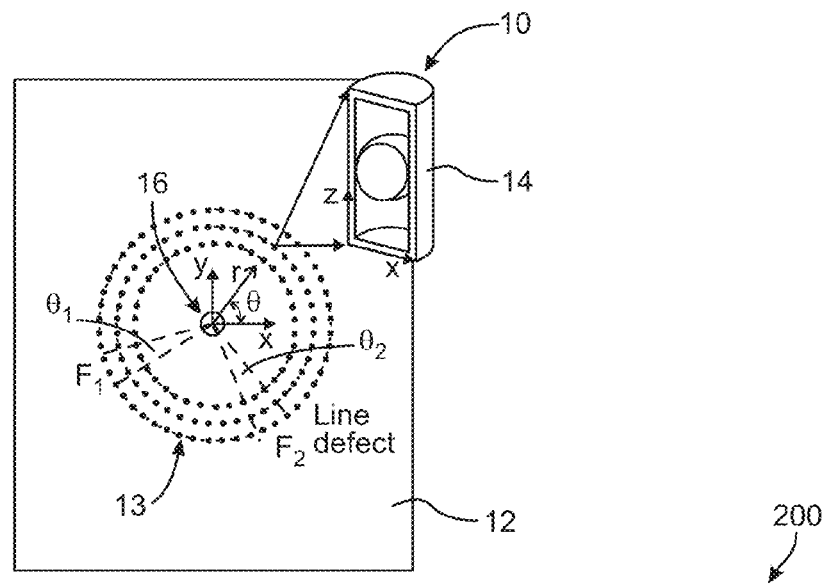
FIG. 1 is a Schematic of the thin aluminum plate with the embedded metamaterial lens in accordance with the teachings of the present invention.

Referring now to FIG. 1, an example of an apparatus 10 with an embedded lens is illustrated. The example apparatus 10 relies on the concept of dynamic structural tailoring of the host structure achieved via acoustic metamaterial based design. By exploiting the characteristic behavior of anisotropic resonant metamaterials, acoustic lenses 13 can be designed and embedded (or surface mounted) into structural elements 14 to mold the ultrasonic wavefronts generated by either a single transducer 16 (during actuation) or by non-linear damage (during sensing).

For example, anisotropic resonant acoustic metamaterials in a fluid background have proven to exhibit collimation and sub-wavelength resolution capabilities due to the characteristic hyperbolic nature of their Equi-Frequency-Contours (EFC). Hyperbolic EFCs is a well-known characteristic of the so-called hyperlenses that enables the conversion of evanescent into propagating waves therefore allowing the projection into the far-field of wave components that otherwise would be lost. The evanescent waves are typically associated with the smallest wavelengths that bring information about the finer spatial details. It follows that these wave components are intrinsically related to the maximum resolution achievable in either an optical or an acoustic image.

Figure 2A:
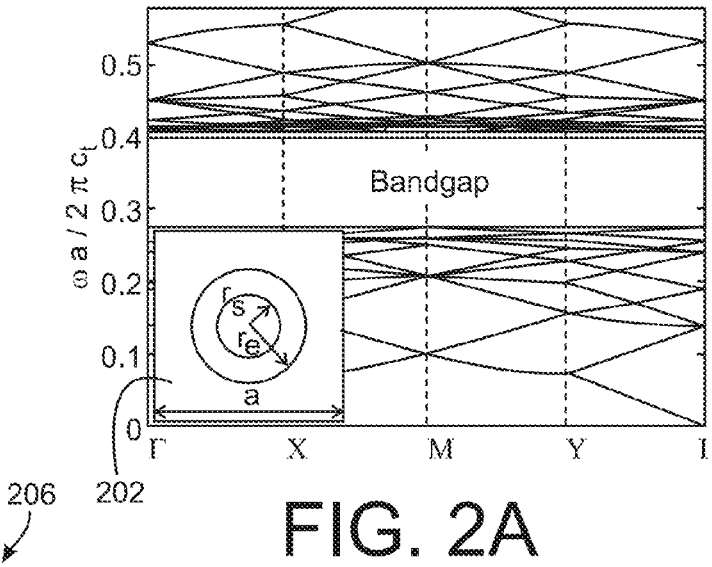
FIGS. 2A and 2B together illustrate dispersion characteristics (SV mode) in the first Brillouin zone of a perfectly periodic (FIG. 2A) and a defected material (FIG. 2B) showing the existence of a full bandgap and the generation of localized modes inside the bandgap due to the defect.
Figure 2B:
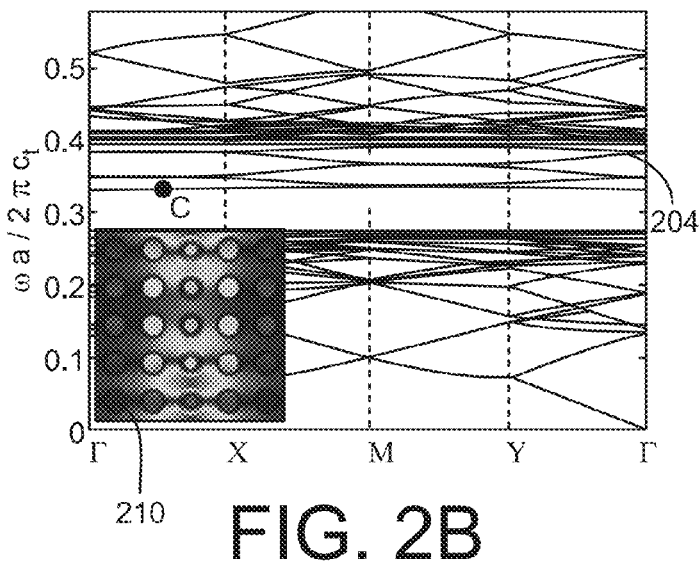

The hyperbolic nature of anisotropic locally resonant metamaterials in conjunction with spatially tailored frequency bandgaps and localized modes may be exploited to design embedded acoustic lenses for selective interrogation. The operating principle is illustrated on bulk materials and then extended to a finite structure for practical application. Considering a bulk perfectly periodic elastic metamaterial with a square lattice structure (lattice constant a) made of an aluminum background and cylindrical steel inclusions ($r_s=0.25a$) coated in silicon rubber ($r_e=0.35a$). The dispersion curves along the irreducible part of the first Brillouin zone is illustrated as curve 200 in FIG. 2A and is calculated by the supercell Plane Wave Expansion method (PWE). The curve 200 shows the existence of a full bandgap for the SV mode in the non-dimensional frequency range $\Omega=\omega a/2\pi c_t=0.27\div0.4$. In this range, propagating waves are not supported therefore the material effectively acts as a mechanical stopband filter. The response of the bulk material in the bandgap can be tailored by exploiting defects that locally break the periodicity of the crystal. Defects are associated with a spatially localized dynamic response which results in additional modes located inside the bandgap. Among the different types of defects, line defects (or waveguides) can be used to create modes inside the bandgap that are spatially confined by the defect but free to propagate inside it. Defects can be created by altering either the geometric or the material properties of one or more inclusions. For the present example, a line defect was created by altering the size of the steel inclusions ($r_s=0.15a$) in the center array of a squared lattice material 202 as depicted in FIG. 2A. The introduction of the line defect 202 resulted in additional localized modes 204 inside the bandgap as illustrated in FIG. 2B, that propagate through the crystal in the direction of the defect, as shown by the modal displacement field 206 in FIG. 2B. These localized modes result in preferential paths of propagation through the crystal at specific frequencies. The inset in FIG. 2A shows the geometric parameters of the unit cell while the inset in FIG. 2B shows the geometry of the supercell and the displacement field of the localized defect mode corresponding to point C. In the present example, a supercell PWE approach to model the locally non-periodic material was utilized. A 5×5 supercell was used for the calculations as shown in the inset 310 in FIG. 3B.

The frequency of the localized modes can be controlled by properly designing the properties of the defect. It follows that the propagation characteristics of a metamaterial can be tailored in both the spatial and frequency domain by designing a network of defects.

The second key characteristic exploited in this disclosure is related to the ability of anisotropic resonant metamaterials to generate hyperbolic Equi-Frequency-Contours (EFC). The direct comparison of the EFC curves for the SV mode (FIG. 3A) of a square lattice a×a resonant metamaterial (isotropic in the long wavelength limit) with a rectangular lattice a×4a resonant metamaterial (anisotropic in the long wavelength limit) shows that the anisotropic nature of the rectangular lattice results in the generation of hyperbolic EFCs.

Figure 3A:
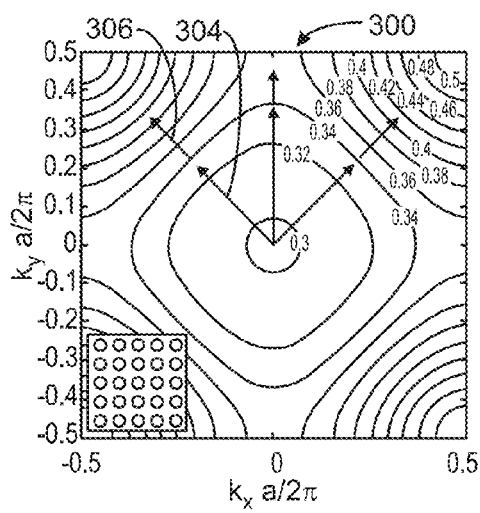
FIGS. 3A and 3B together illustrate a comparison of the Equi-Frequency-Contours for the isotropic (FIG. 3A) and anisotropic (FIG. 3B) resonant metamaterial.
Figure 3B:
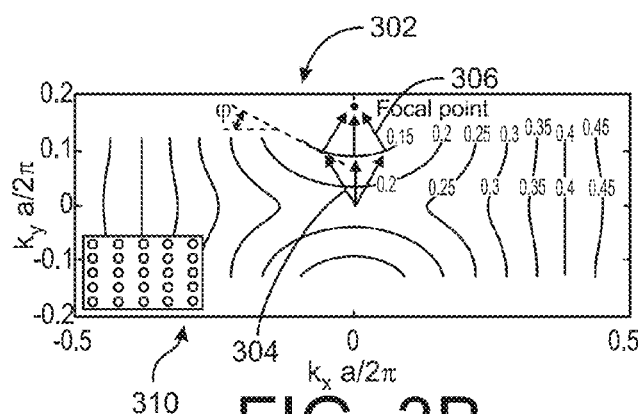

FIGS. 3A and 3B together illustrate a comparison of the Equi-Frequency-Contours for the isotropic 300 (FIG. 3A) and anisotropic 302 (FIG. 3B) resonant metamaterial. The superimposed schematic shows that for the hyperbolic EFCs (FIG. 3B) the initial direction of propagation of the incident wave 304, indicated by the wavevector, is steered to become orthogonal to the EFC branches 206, that is the direction of the group velocity. Therefore, the initially diffused field is focused at the focal point of the hyperbola as it travels through the crystal.

Depending on the specific design of the hyperbolic EFCs and on the location of the focal point, the metamaterial will act either as a focusing or a collimating lens for incident ultrasonic waves. In fact, an incident wave initially emitted in the direction indicated by the wavevector 304 is redirected so that in the far-field the group velocity becomes orthogonal to the EFCs 306. Therefore, an initially diffused field propagating through an anisotropic crystal with hyperbolic EFCs will be converted into a focused wave field while travelling through the crystal. The location of the focal point depends on the specific design of the lattice structure (that ultimately affects the shape of the hyperbolic EFCs) and on the selected frequency of excitation. In the limit case of a flat EFC, the focal point of the hyperbola moves to infinity therefore originating, in the far-field, a perfectly collimated wave field.

The above described characteristics of anisotropic resonant metamaterials can be exploited in the design of embedded lenses for SHM applications. For instance FIG. 1 illustrates a thin aluminum plate 12 with the embedded metamaterial lens 13. Selected sectors of the lens at prescribed azimuthal locations $\theta_i$ can be tailored to create localized modes (using line defects) at selected frequencies $f_i$ inside the bandgap.

In particular, the anisotropic metamaterial lenses 13 with spatially tailored line defects can be used to create focused (or collimated) and steerable excitation by using a single ultrasonic transducer. This is illustrated using a 2 m×2 m simply supported thin aluminum plate 12 with a thickness t=4 mm. The inclusions are represented by mass-in-mass systems. The overall structure is modeled according to the Kirchhoff's thin plate theory with attached lumped single degree of freedom resonators. Note that the use of Kirchhoff's theory is justified because the model will be used for the low frequency-thickness range where the through-the-thickness distribution of the out-of-plane displacement associated with the $A_0$ mode is practically constant.

The governing equation of the plate is discretized using the assumed modes method and solved by direct time integration using a $4^{th}$ order Runge-Kutta scheme. In this approach, it is assumed the displacement field expressed as $w=\Sigma_i\phi_i(x, y)q_i$ where $\phi_i$ is a set of basis functions and $q_i$ are generalized coordinates. Upon discretization, the resulting system of governing equations is given by:

$$M_s^{pq}\ddot{q}_s(t) + C_s^{pq}\dot{q}_s(t) + K_s^{pq}q_s(t) + k_R\left[\sum_{pq}\varphi_{pq}(x_R^r, y_R^r)q_s(t) - q_R(t)\right]\varphi_{pq} = \varphi_{pq}(x_R, y_R)F(t) \quad (1)$$

$$m_R^r\ddot{q}_R^r(t) + k_R^r\left[q_R^r(t) - \sum_{pq}\varphi_{pq}(x_R^r, y_R^r)q_s(t)\right] = 0 \quad (2)$$

with p=1 ... n, q=1 ... m, and r=1 ... L. Eqns. (1) and (2) represent a n×m×L system of second order coupled ordinary differential equations where $M_s^{pq}$, $C_s^{pq}$ and $K_s^{pq}$ are generalized mass, damping and stiffness matrices of the plate associated with the pth×qth assumed modes, $q_s(t)$ and $q_R(t)$ are the generalized coordinates of the plate and of the local resonators, $m_R^r$ and $k_R^r$ are the mass and stiffness of the resonator, $\phi_{pq}$ is the set of basis functions that in this analysis is defined as the eigenmodes of the thin plate structure. A 2% loss factor was also applied to the plate in order to simulate the inherent structural damping of aluminum. In particular, $C_s^{pq}$ was expressed in Rayleigh form C=αM+βK with the mass proportional coefficient α=0 and the stiffness proportional coefficient β=$10^{-6}$. Note that, in the frequency range retained for this study, the low structural damping results in decay lengths of several meters for the fundamental longitudinal and shear modes. Therefore, the effect of absorption is negligible.

The model described by Eqns. (1) and (2) is used to illustrate the three main characteristics of the embedded resonant lens: (1) beam-forming, (2) beam-steering, and (3) sub-wavelength resolution. These characteristics are shown using three separate examples.

In the first example, an example plate was equipped with a semi-circular anisotropic resonant metamaterial lens with n=6 layers and a line defect located at θ=90°. The line defect was created by altering the stiffness properties of the inclusions in a 20°-wide sector centered at the geometric center of the lens (see FIG. 1). The inclusions non-dimensional mass ratio was set to $m_r = M_{Resonator}/m_{Plate} = 6 \times 10^{-3}$ while the spacing to $s_r = 0.02$ m and $s_\theta = s_r/2 = 0.01$ m in the radial and azimuthal directions, respectively. The stiffness of the inclusions in the line defect was set to $0.2 \times 10^9$ N/m (from the initial $0.6 \times 10^9$ N/m) resulting in an uncoupled frequency of the individual resonator of $f_{90°} = 5.032$ kHz.

Figure 4A:
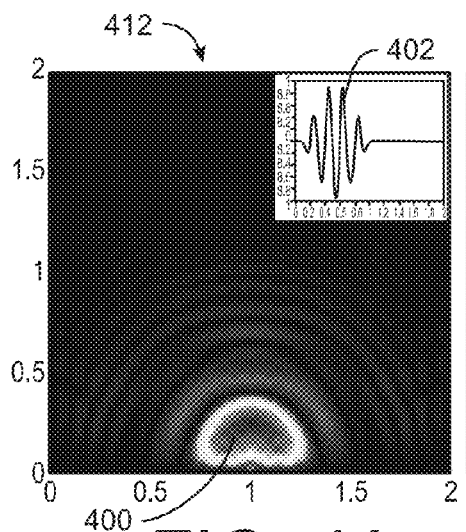
FIG. 4A-4D together illustrate maps of the particle displacement squared showing the performance of a spatially tailored resonant anisotropic metamaterial lens embedded in a thin simply supported aluminum plate.

In one example, the source 400, located in the center of the lens (FIG. 4A), was used to generate a 5.5 period Hanning-windowed force tone burst 402 with amplitude F=1N and it was tuned at the fundamental frequency $f_{90°}$ of the line defect. Numerical results, given in terms of squared particle displacement, show that the lens is able to convert the omni-directional wave produced by the single actuator into an ultrasonic beam 410 (FIG. 4B) that remains collimated upon propagation in the plate. Without the lens the point excitation would produce a diffused wave field 412 as shown in FIG. 4A. Note that the combined use of line defects and hyperbolic EFCs allows achieving a high degree of collimation thanks to the bandpass filtering effect produced by the waveguide. Given an omni-directional source, such as the point source considered in this study, the waveguide bandpass filters wavevector components having direction closely aligned with the axis of the guide. These components are successively collimated by the hyperbolic EFC. Based on this mechanism, it can be highlighted that the width of the collimated beam is mostly controlled by the width of the waveguide, therefore narrower beams could be obtained by designing waveguides operating at higher excitation frequencies. The angle of divergence ϕ of the collimated beam is controlled, other than from the bandpass character of the waveguide, from the local slope of the EFCs at the point of intersection with the wavevector (see FIGS. 3A, 3B).

The concept of line defect can also be exploited to steer the excitation beam. The lens can be spatially tailored in the azimuthal direction by embedding multiple line defects tuned at different frequencies. Each line defect is associated with well defined localized modes in the bandgap and can be activated by tuning the frequency of the excitation at the corresponding frequency of the defect. This concept is schematically illustrated in FIG. 1 where two sectors of the lens, centered at $\theta_1$ and $\theta_2$, are designed to host line defects associated with localized modes at frequencies $f_1$ and $f_2$. The previously developed thin plate model was used to numerically investigate this design. Two 20°-wide sectors centered at $\theta_1 = 45°$ and $\theta_2 = 135°$ and tuned at $f_1 = 1.125$ kHz and $f_2 = 7.957$ kHz were embedded in a circular lens located in the center of the plate. The inclusions non-dimensional mass ratio was set to $m_r = M_{Resonator}/m_{Plate} = 6 \times 10^{-4}$ while the spacing to $s_r = 0.04$ m and $s_\theta = s_r/2 = 0.01$ m. The lens was made of n=7 layers. The lumped stiffness of the inclusions in the two sectors was set to $k_1 = 1 \times 10^6$ N/m and $k_2 = 5 \times 10^7$ N/m that resulted in fundamental uncoupled frequencies of the inclusions equal to $f_1$ and $f_2$, respectively.

Figure 4B:
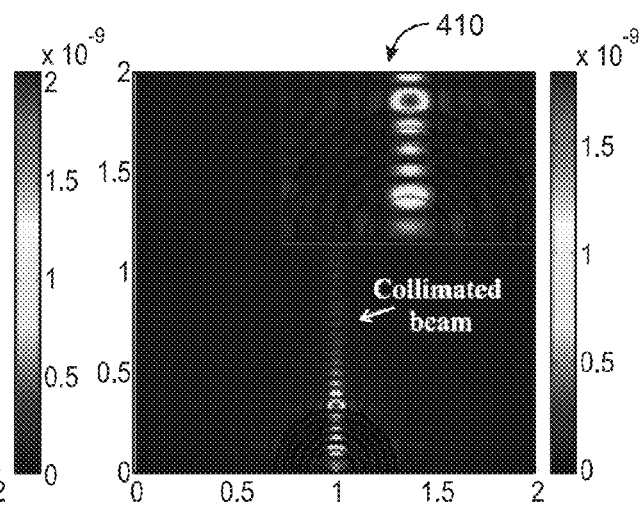
Figure 4C:
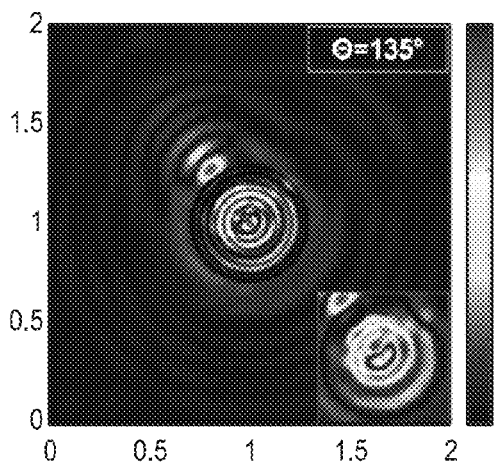
Figure 4D:
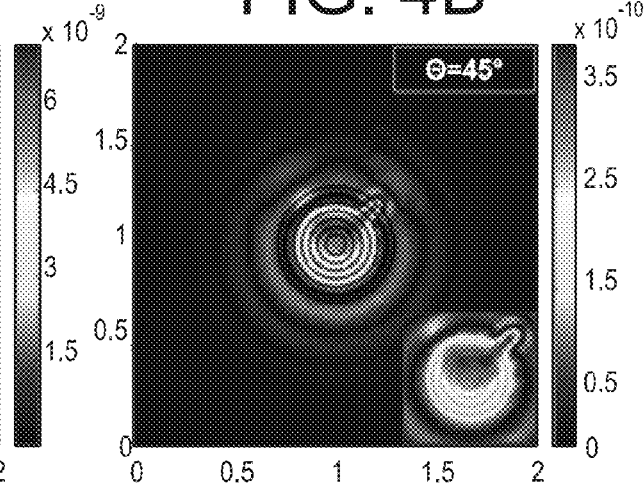

FIG. 4B shows the formation of the collimated beam due to a spatially tailored bandgap located at θ=90°. The beam remains well collimated upon propagation in the host structure. Without the lens the source produces a diffused wave field as in FIG. 4A. FIGS. 4C and 4D show that by exploiting the concept of spatially tailored bandgap the ultrasonic beam can also be steered by simply controlling the excitation frequency. The beam at $\theta_1 = 45°$ is triggered by an excitation at $f_1 = 1.125$ kHz while the beam at $\theta_2 = 135°$ is triggered by an excitation at $f_2 = 7.957$ kHz.

The center frequency of the tone burst force excitation with amplitude F=1N was tuned first at $f_1$ and then at $f_2$. Numerical simulations (see FIGS. 4C, 4D) clearly show that the lens design is able to generate an ultrasonic beam in the predefined direction by simply tuning the frequency of the excitation. It will be appreciated that the spatial tailoring of the bandgap can be implemented over the 360° span of the lens to achieve full control on the direction of the beam as desired. In this design, the angular resolution of the lens will be limited by the intrinsic width of each waveguide which is related to the operating frequencies. Therefore, it can be understood that lenses designed for a higher frequency range can achieve a progressively finer angular resolution.

Embedded metamaterial lenses can also be used as a tool to increase the sensitivity during the damage sensing phase. In particular, anisotropic lenses can be used to achieve sub-wavelength resolution (beyond the diffraction limit) to clustered incipient damage. Incipient damage is known to induce nonlinear harmonic response when excited by an intense ultrasonic field. Several studies have exploited this characteristic nonlinear response to perform remote damage identification and localization. In case of clustered incipient damage, the narrow spacing between the nonlinear damage (sources) does not allow discerning their individual location from measurements performed in the far-field, where sensors are typically located. The reconstructed damage appears as an aggregate with an overestimated footprint and without meaningful information on the damage shape (useful for damage classification). This limited resolution is the result of a well-known physical phenomenon in optics and acoustics: the Abbe diffraction limit. In an acoustic image, the finer details (smaller than the characteristic wavelength at the frequency of interest) are associated with the evanescent waves generated upon diffraction of the incident wave from the scatterer. The diffracted evanescent waves decay exponentially in the near-field leading to a loss of information. It is this lost information, in fact, that limits the spatial resolution of sensors located in the far-field. Anisotropic metamaterials can convert evanescent into propagating waves and project them into the far-field. This concept is extended to finite elastic structures in order to obtain sub-wavelength resolution of incipient damage. The performance of the lens is illustrated by using the embedded semi-circular design previously discussed. In this case, no spatial tailoring is needed (uniform inclusions were used throughout the lens). The lens is tested by using two acoustic sources (simulating incipient damage) at a selected frequency $f_d$=5.032 kHz. The two damage (sources) are separated by a distance $\Delta s$=0.05 m along the x-axis. This distance corresponds to about $0.4\lambda$, where $\lambda$ is the wavelength of the $A_0$ (Lamb) mode of the flat plate at the selected frequency. It will be observed that this is a conservative estimate of $\lambda$ because the calculation does not take into account the additional mass of the inclusions which would result in a longer effective wavelength. Therefore the expected sub-wavelength resolution is at least $0.4\lambda$.

Figure 5A:
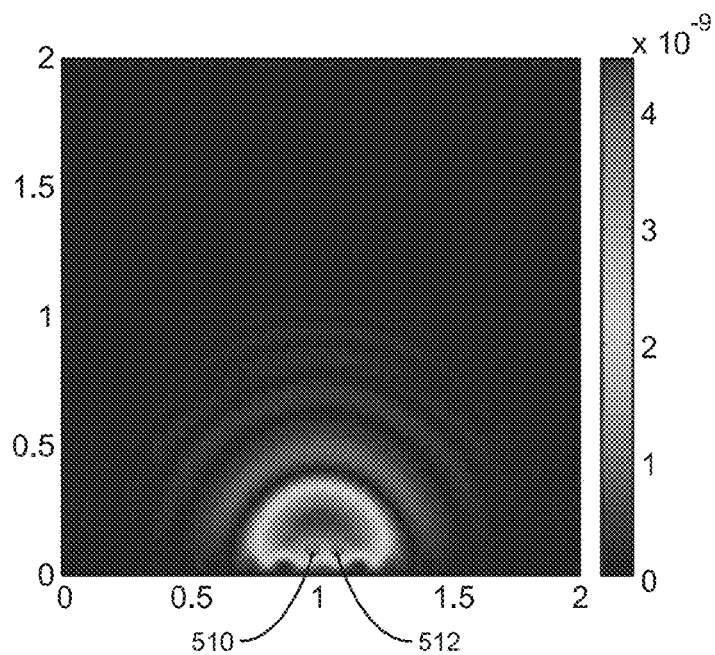
FIGS. 5A and 5B illustrate numerical results showing the sub-wavelength resolution capability in a thin plate with an embedded metamaterial lens.
Figure 5B:
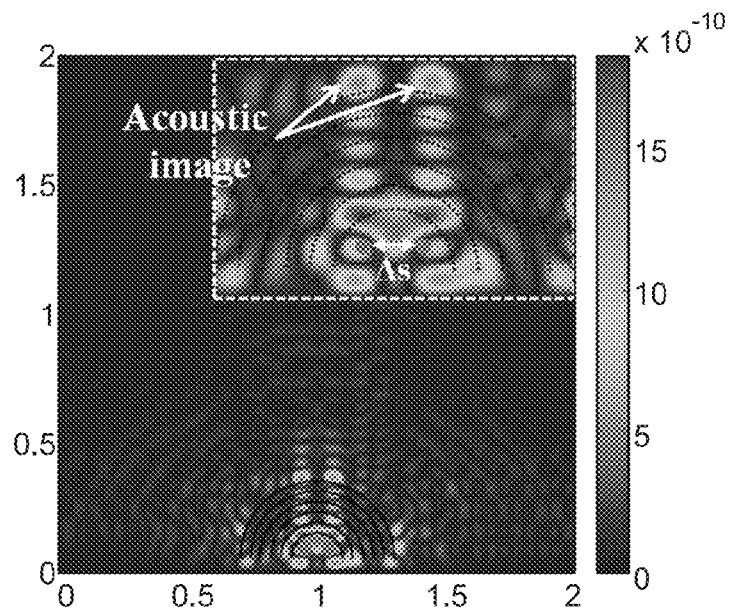

The results illustrated in FIG. 5B clearly show that the lens is able to project a distinct image of the two sources in the far-field, therefore achieving a spatial resolution of at least $0.4\lambda$ that is beyond the diffraction limit.

FIGS. 5A and 5B illustrate numerical results showing the sub-wavelength resolution capability in a thin plate with an embedded metamaterial lens. In the illustrated example, two acoustic sources 510, 512 are separated by a distance smaller than the diffraction limit. FIG. 5A illustrates the results without the lens the two sources generate a diffused field with no information about the individual sources. FIG. 5B illustrates the results with the lens, wherein a distinct image of the original sources is projected to the far-field providing resolution beyond the diffraction limit.

The response of the plate without the lens (FIG. 5A) is also provided for comparison. In this case, the two sources produce a diffused field where the information on the individual sources is lost. Note that, contrarily to previous studies showing radial canalization effects, this lens design produces parallel magnification of the sources. This is due to the fact that the plate acts as a waveguide whose dynamic properties are tailored by the attached local resonators. The effect of these inclusions is essentially inertial while the typical canalization effect is mostly impedance driven. In this design, the inertia-generated anisotropy determines the direction of propagation in the underlying waveguide while the resonant character of the inclusions determines the hyperbolic characteristic of the lens.

It will be noted that the lens design used in the above simulations was not optimized to achieve maximum performance. Therefore, it can be appreciated that higher level of sub-wavelength resolution can be obtained by proper optimization of the design parameters. In particular, the optimization can concern the shape of the unit cell (which controls the lens anisotropy and the hyperbolic nature of the EFCs) and the mass ratio of the resonant inclusions (which controls the activation frequency of the line defects).

As such, the present disclosure concerns a numerical investigation on the use of locally resonant acoustic metamaterial lenses embedded in plate-like structural elements to achieve selective interrogation with a single ultrasonic transducer. The lens was designed based on the concept of locally resonant anisotropic metamaterials combined with the ideas of spatially tailored bandgaps and localized modes. The example design was able to achieve selective interrogation as well as focusing or collimation depending on the selected excitation frequency. In particular, the combined use of waveguides and hyperbolic EFCs allowed obtaining narrow ultrasonic beams with a high degree of collimation. The use of tuned spatially tailored waveguides also allowed achieving beam-steering by simply controlling the frequency of the excitation of the single transducer. In addition, in at least one example, the use of the acoustic lens to achieve high spatial resolution to clustered acoustic sources, such as those produced by nonlinear damage, is disclosed. Numerical results show that the lens can achieve sub-wavelength resolution projecting into the far-field a distinct image of acoustic sources that are separated by a distance beyond the diffraction limit.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents.

We claim:

1. A metamaterial based acoustic lens for structural health monitoring comprising:
   a transducer;
   a thin plate; and
   a metamaterial lens embedded within the thin plate, wherein the plate is positionable such that the metamaterial lens at least partially overlays the transducer;
   wherein selected sectors of the metamaterial lens at prescribed azimuthal location include line defects to create localized modes at selected frequencies inside the bandgap.

2. A metamaterial based acoustic lens as recited in claim 1, wherein the thin plate is an aluminum plate.

3. A metamaterial based acoustic lens as recited in claim 1, wherein the line defects are located at ninety degrees.

4. A metamaterial based acoustic lens as recited in claim 3, wherein at least one of the line defects is created by altering the stiffness properties of the inclusions in a 20°-wide sector centered at the geometric center of the metamaterial lens.

* * * * *